United States Patent
Jolly et al.

(10) Patent No.: US 9,758,931 B2
(45) Date of Patent: Sep. 12, 2017

(54) ONLINE TREATED SEALABLE AND PEELABLE MEDICAL PAPER FOR MEDICAL STERILIZATION PACKAGING

(71) Applicant: MONDI AG, Vienna (AT)

(72) Inventors: Agnes Jolly, La Murette (FR); Tiina Olkkonen, Helsinki (FI); Peter Putz, Bad (AT); Kalle Miettinen, Helsinki (FI); Heikki Järvinen, Lohja (FI)

(73) Assignee: MONDI AG, Vienna (AT)

( * ) Notice: Subject to any disclaimer, the term of this patent is extended or adjusted under 35 U.S.C. 154(b) by 0 days.

(21) Appl. No.: 14/441,743

(22) PCT Filed: Nov. 9, 2012

(86) PCT No.: PCT/EP2012/072213
§ 371 (c)(1),
(2) Date: May 8, 2015

(87) PCT Pub. No.: WO2014/071986
PCT Pub. Date: May 15, 2014

(65) Prior Publication Data
US 2015/0305814 A1 Oct. 29, 2015

(51) Int. Cl.
*D21H 19/84* (2006.01)
*D21H 25/08* (2006.01)
(Continued)

(52) U.S. Cl.
CPC ............ *D21H 19/84* (2013.01); *A61B 50/30* (2016.02); *D21H 17/28* (2013.01); *D21H 17/34* (2013.01);
(Continued)

(58) Field of Classification Search
CPC .......... A61B 50/30; A61L 2/26; D21H 27/10; D21H 23/48; D21H 23/50; D21H 17/28;
(Continued)

(56) References Cited

U.S. PATENT DOCUMENTS 4,728,396 A * 3/1988 Alheid ................ D21H 5/0005
162/191
5,641,387 A * 6/1997 Baldini ................ D21H 23/22
162/136
(Continued)

OTHER PUBLICATIONS

Lipponen, Surface Sizing with Starch Solutions at High Solids Content, Helsinki University of Technology, Jan. 28, 2005 [http://lib.tkk.fi/Diss/2005/isbn9512274914/isbn9512274914.pdf].*
(Continued)

*Primary Examiner* — Eric Hug
(74) *Attorney, Agent, or Firm* — B. Aaron Schulman, Esq.; Stites & Harbison, PLLC

(57) ABSTRACT

A method and apparatus for manufacturing medical paper for medical sterilization packaging, medical paper and medical sterilization packaging are disclosed. A paper web is formed of fibrous substrate comprising cellulosic fibers and optionally synthetic fibers, with opposite first and second sides. On-line with the forming of the paper web, reinforcing material is applied on the first side and pressed into structure of the paper web such that delamination resistance of the structure is increased. Sealing material is applied on the second side of the paper web on-line with the forming of the paper web.

15 Claims, 1 Drawing Sheet

(51) Int. Cl.
*D21H 23/48* (2006.01)
*D21H 23/50* (2006.01)
*D21H 23/70* (2006.01)
*D21H 27/10* (2006.01)
*D21H 17/28* (2006.01)
*D21H 17/34* (2006.01)
*D21H 17/36* (2006.01)
*D21H 17/37* (2006.01)
*D21H 17/57* (2006.01)
*D21H 17/60* (2006.01)
*D21H 19/18* (2006.01)
*D21H 19/20* (2006.01)
*D21H 21/16* (2006.01)
*D21H 21/20* (2006.01)
*D21H 23/36* (2006.01)
*D21H 25/00* (2006.01)
*A61B 50/30* (2016.01)
*D21H 13/16* (2006.01)
*D21H 17/17* (2006.01)
*D21H 17/53* (2006.01)
*D21H 17/62* (2006.01)
*B65D 75/32* (2006.01)

(52) U.S. Cl.
CPC .............. *D21H 17/36* (2013.01); *D21H 17/37* (2013.01); *D21H 17/57* (2013.01); *D21H 17/60* (2013.01); *D21H 19/18* (2013.01); *D21H 19/20* (2013.01); *D21H 21/16* (2013.01); *D21H 21/20* (2013.01); *D21H 23/36* (2013.01); *D21H 23/48* (2013.01); *D21H 23/50* (2013.01); *D21H 23/70* (2013.01); *D21H 25/005* (2013.01); *D21H 27/10* (2013.01); *B65D 75/326* (2013.01); *D21H 13/16* (2013.01); *D21H 17/17* (2013.01); *D21H 17/53* (2013.01); *D21H 17/62* (2013.01)

(58) Field of Classification Search
CPC ........ D21H 17/34; D21H 17/36; D21H 17/37; D21H 17/57; D21H 17/60; D21H 17/62; D21H 17/53; D21H 17/17; D21H 23/36; D21H 23/70; D21H 21/20; D21H 19/18; D21H 19/20; D21H 19/84; D21H 21/16; D21H 25/08; D21H 25/12; D21H 25/14; B65D 65/42; D21F 9/00; D21F 9/02; D21F 11/00; D21F 11/02
USPC ...... 162/134–137, 265, 266; 428/195.1, 343, 428/352–354; 427/209–211, 121, 288, 427/326, 361, 382, 391, 394, 395, 411; 206/438–441, 828
See application file for complete search history.

(56) References Cited

U.S. PATENT DOCUMENTS

| | | | |
|---|---|---|---|
| 6,156,677 A | 12/2000 | Brown Reed et al. | |
| 6,284,097 B1* | 9/2001 | Wulz | D21H 23/72 162/137 |
| 6,368,459 B1* | 4/2002 | Kinnunen | D21H 23/70 118/60 |
| 6,808,691 B1* | 10/2004 | Herve | A61L 2/26 206/363 |
| 8,927,073 B2* | 1/2015 | Zhou | B41M 5/504 162/137 |
| 9,580,628 B2 | 2/2017 | Tripier et al. | |
| 2002/0168508 A1 | 11/2002 | Reed et al. | |
| 2007/0246377 A1* | 10/2007 | Paris-Jolly | A61L 2/26 206/210 |
| 2008/0166262 A1* | 7/2008 | Deka | A61L 2/202 422/28 |
| 2009/0151883 A1* | 6/2009 | Nomura | D21H 23/34 162/136 |
| 2013/0252496 A1 | 9/2013 | Tripier et al. | |

OTHER PUBLICATIONS

International Search Report for PCT/EP2012/072213 dated Jun. 7, 2013.

* cited by examiner

Fig. 1    100
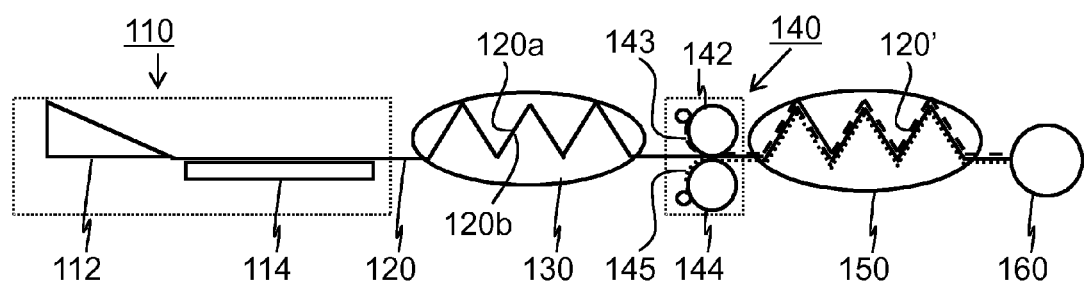
Fig. 2    200
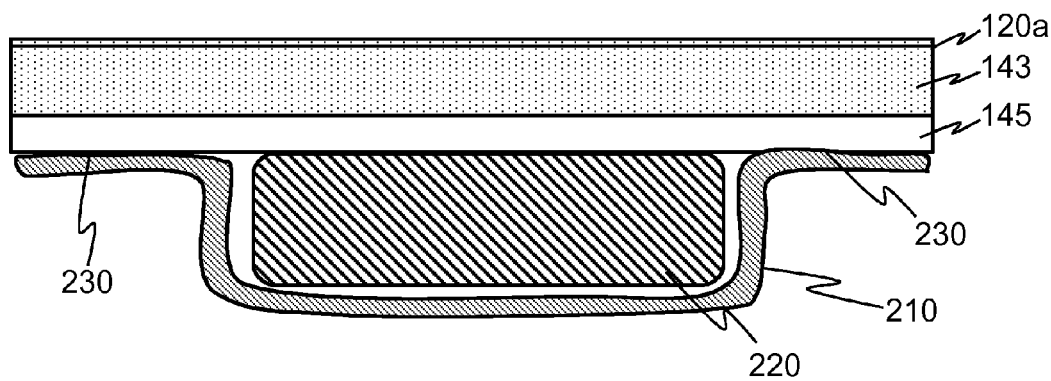
Fig. 3    200
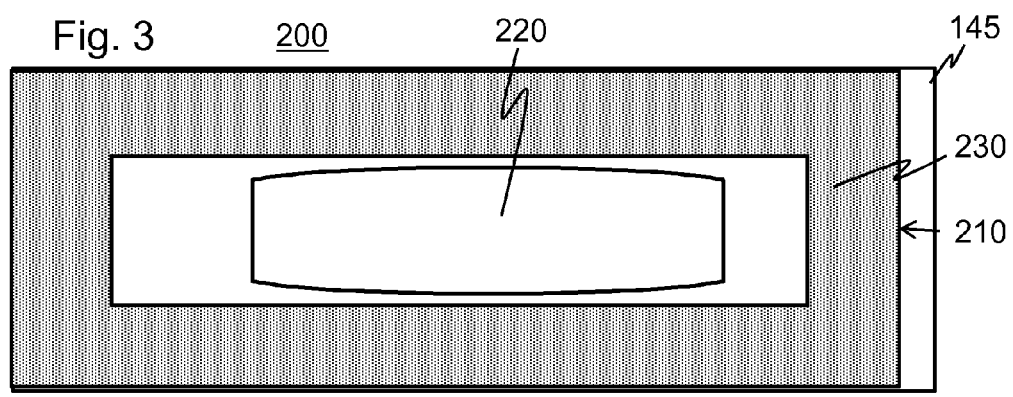

ONLINE TREATED SEALABLE AND PEELABLE MEDICAL PAPER FOR MEDICAL STERILIZATION PACKAGING

TECHNICAL FIELD

The present invention generally relates to online treated sealable and peelable medical paper for medical sterilization packaging.

BACKGROUND ART

Medical sterilization packaging is needed for storage and transport of various sterilized medical devices. NF EN ISO 11607-1 July 2006 describes in annex A various factors influencing the design of the medical sterilization packaging or medical packaging system using terminology of this standard. Typical sterilization processing is performed by ethylene oxide gas (EO), gamma irradiation (γ), electron beam (e-beam), steam autoclaving, or low-temperature oxidative sterilization processes. If sterilized is to be performed by EO, steam, or oxidizing processes, the packaging is provided with a sterile barrier system that has a permeable component to allow the sterilizing gases to enter, kill the microorganisms, and escape without significant residual concentrations. The sterile barrier system has, in majority of cases, "a top-web", a "bottom web", and a means to join the webs together. In the case where a peelable seal is required, a sealant layer is applied to allow sealing of the two layers together. The sealant layer, typically produced by off-line coating, has traditionally been applied to the permeable web. Today, many films incorporate the sealant layer as (a) layer(s) in the film construction. Where a weld seal is required, compatibility of the webs is required to allow joining by heat or pressure.

The sterile barrier system porous web is often made of medical paper that is manufactured to be free of contaminants or micro-organisms and that has been processed to close large pores that could pass micro-organisms while leaving sufficient permeability for the sterilisation agents such as the EO gas. Medical papers should meet predetermined minimum physical requirements such as air permeance, tensile strength, tear resistance, and burst strength. Various other requirements are also set in paragraphs 5.1.7 and 5.1.9 of the aforementioned ISO standard. The latter paragraph sets requirements for the sealing if any is formed and for the peel-open characteristics. The peel-open shall be continuous and homogenous without delamination or tearing of the material that can affect aseptic opening and presentation. Other requirements such as microbial barrier properties are also defined by the ISO standard in question.

Sealable and peelable medical paper for medical sterilization packaging are produced using off-line or on-line processing. On-line processing removes the need for a subsequent process step and saves energy while adding complexities and particular requirements for reliability of the processing to avoid producing of waste and consuming energy. For example, WO0231248 (A2) discloses a method of producing such paper by impregnating or saturating the paper web by mixing in the pulp a composition comprising a drapable saturant component and an additional saturant polymer. The composition should provide an enhanced seal strength between the fibrous web and a base component polymeric material. By saturating the paper it is desired to enable sealing directly to materials used in the base components of the paper web so that separate off-line coating is not needed. The saturating of the paper with such compositions yet consumes relatively large amounts of technical chemicals that are more expensive than the normal source materials of paper. Moreover, such polymers may be produced from oil and hinder recycling of the paper for production of other grades of paper or board with commercially applicable paper recycling technologies.

Off-line coating based methods may provide more efficient use of renewing natural materials. In one technique, instead of pulp additive based impregnation, a paper web in a paper machine is first formed, dried and on-line sized by applying some binder with a size press on both sides of the paper web as the size press on operation forms a pond of the binder material on both sides of the web and these ponds mix freely at both edges of the web. The paper web is then dried and rolled into machine rolls. Subsequently, a heat sealing layer is off-line coated onto the paper web. The on-line application of the binder helps to avoid tear, so releasing of fibres, especially cellulosic material that can affect the aseptic opening and presentation of packaged medical objects, as the heat-sealing layer is formed onto a reinforcing material layer. The peeling occurs within the heat-sealing layer and/or on the interface between the heat-sealing layer and the reinforcing material layer. It is yet desirable to avoid the off-line coating as a relatively expensive procedure.

One known technique for forming peelable medical papers for medical sterilized packaging applies the heat-sealing layer onto the paper web by using off-line extrusion of polyethylene.

An object of the invention is to provide ecological and economical sealable and peelable medical paper for medical sterilization packaging and packaging containing same, to eliminate or mitigate some drawbacks relating to prior known such papers and packages and the production of the same, or to provide a new technical alternative.

SUMMARY

According to a first example aspect of the invention there is provided a method for manufacturing medical paper for medical sterilization packaging, the method comprising:

forming a paper web of fibrous substrate comprising cellulosic fibres, the paper web comprising opposite first and second sides;

on-line with the forming of the paper web, applying reinforcing material on the first side and pressing the reinforcing material into structure of the paper web such that delamination resistance of the structure is increased; and on-line with the forming of the paper web, applying sealing material on the second side the paper web.

In this document, term "paper" refers to a sheet of wet-laid material that comprises cellulosic fibres and optionally up to 30 wt % synthetic fibres, in a structure in which the fibres are bonded to each other forming a paper-like structure. The synthetic fibres may be synthetic staple fibres.

The paper web may consist of a single layer of the fibrous substrate.

The forming may be performed using a forming section. The forming section may comprise at least one of a Fourdrinier wire; a gap former; a suction box; and a water removal foil.

According to a second example aspect of the invention there is provided a paper making apparatus, comprising:

a forming section configured to form a paper web of fibrous substrate comprising cellulosic fibres, the paper web comprising opposite first and second sides;

an on-line reinforcing material applicator configured to apply reinforcing material on the first side;

an on-line press configured to press the reinforcing material into structure of the paper web such that delamination resistance is increased throughout the structure of the paper web; and an on-line sealing material applicator configured to apply sealing material on the second side the paper web.

The on-line reinforcing material applicator, the on-line sealing material applicator and the on-line press may be parts of same surface treatment station.

According to a third example aspect of the invention there is provided medical paper of fibrous substrate comprising cellulosic fibres, for medical sterilization packaging, the paper having opposite first and second sides and comprising:

reinforcing material applied through the first side into structure of the paper such that delamination resistance is increased throughout the structure of the paper web by application from the first side and in result the paper has uneven z-directional distribution of the reinforcing material; and sealing material on the second side the paper.

According to a fourth example aspect there is provided a medical sterilization packaging comprising:

medical paper of the third example aspect; and a packaging element configured to cover a medical device sealed to the medical paper through the sealing material applied to the second side of the paper.

According to a fifth example aspect there is provided a system comprising:

medical sterilization packaging of the fourth example aspect; and a medical device sealed to into the packaging by the sealing material applied to the second side of the paper.

Different non-binding example aspects and embodiments of the present invention will be presented in following detailed description and in appended dependent claims. It should be appreciated that corresponding embodiments may be freely applied to other embodiments and example aspects.

BRIEF DESCRIPTION OF THE DRAWINGS

Some example embodiments of the invention will be described with reference to the accompanying drawings, in which:

FIG. 1 shows a schematic picture of some basic elements of a paper machine according to an embodiment of the invention;

FIG. 2 shows a medical sterilization packaging with a medical device therein, seen as a cross-section, with greatly exaggerated thicknesses for illustration purposes; and FIG. 3 shows the medical sterilization packaging of FIG. 2 seen as from bottom.

DETAILED DESCRIPTION

In the following description, like reference signs denote like elements.

FIG. 1 shows a schematic picture of some basic elements of a paper machine 100 according to an embodiment of the invention. The paper machine 100 comprises a forming section 110 with a headbox 112 and a wire section 114. The forming section 112 receives pulp that is a water suspension of fibres and optional fillers and other materials and forms paper web 120 by wet laying the fibres in the pulp. The paper web has a first side 120a and a second side 120b. In this example, the first side 120a is referred to as a functional side. Notice that the first side need not be on top as shown in FIG. 1 for illustration purpose only.

The paper machine 100 further comprises a first drying section 130 that removes water from paper web 120 by using e.g. by squeezing out (press nip, for instance) and by evaporating (hot cylinders, infared dryers, for instance).

Downstream from the first drying section, the paper machine 100 comprises a surface treating station 140 comprising a first surface treating unit 142 and a second surface treating unit 144 for processing the paper web 120 through its respective first and second sides to convert the paper web 120 to a processed or surface treated paper web 120'.

It is understood that the usual changes in the paper web caused by drying and calendering, for example, are not accounted for by denoting different reference signs to the paper web while naturally the structure and particularly water content is being continually changed. Moreover, in this context, the term "side" can be understood as "surface". Further, it shall be understood that the orientations and positions of various elements such as the surface treating station are freely adjustable within the known limits of each technique. For instance, the surface treating station 140 be so that the paper web passes through it vertically, horizontally or obliquely, and the paper web may also turn on entering the surface treating station 140 and/or on leaving the surface treating station 140.

The first surface treating unit 142 and the second surface treating unit 144 apply on the first and second sides 120a, 120b of the paper web 120 respective reinforcing material 143 and sealing material 145. The paper web 120 then goes through a press nip in which the reinforcing material 143 is pressed into the paper web 120. Surprisingly, it has been realised that within the paper web 120, the reinforcing material 143 can increase delamination resistance of throughout the paper web even when applied only through one side of the paper web. This is believed to be caused by a mechanism in which the reinforcing material penetrates under pressure induced by the press nip into voids within the structure of the paper web and partly diffuses with any free water i.e. water that resides between the fibres and other particles of the paper web 120.

The surface treating station 140 is, for example, a film transfer station. In alternative other example embodiments, the surface treating station 140 comprises one or more units selected from: a spray coating unit; an air-doctor coating unit; and a curtain coating unit and a pressing unit for pressing the reinforcing material 143 into the web 120.

After the surface treating station i.e. downstream thereof the paper machine 100 comprises a second drying section 150 and a winder 150 for winding in the surface treated paper web 120'.

In a preferred example embodiment, the paper web is surface treated only once with the surface treating station 140 so that one press nip simultaneously presses the reinforcing material 143 and the sealing material 145. In this way, the paper machine need not contain more than two drying sections.

It is to be understood that each of the described sections are on-line units. In other words, these units operate on paper while it is being formed in the paper machine, or the paper is not transferred on a machine roll or winder roll, for example, to off-line processing.

The forming section 110 as well as other main parts of the paper machine are configured using ordinary paper making knowledge considering the paper grade in question and available resources.

In the example embodiment illustrated by FIG. 1, one surface treating station 140 is provided. In another example embodiment, two or more surface treating stations are provided, each followed by a down-stream drying section. The surface treating stations can be of same or different type. In the multi-station embodiment, only one side of the paper web 120 can be surface-treated at one or more surface treating stations, possibly at each of the surface treating stations.

In a further example embodiment with two or more surface treating stations, first a two-sided reinforcement treating is performed in one or more steps with emphasis on the first side 120a with e.g. 80-20 or 70-30 distribution so that the reinforcement material 143 pressed through the first side can increase the delamination resistance throughout the structure of the paper web 120 while further reinforcement material is entered into the structure of the paper web 120 from the second side. The second side of the paper web 120 is subsequently surface treated with the sealing material 145.

The paper machine 100 also comprises in one example embodiment one or more machine calenders before one or more sizing or coating stations.

The paper machine 100 is configured to produce heat sealable paper for medical packaging to allow sterilization and to maintain sterility of the packed medical device (MD) until the end of use. It has to provide a suitable seal strength to avoid any accidental opening of the pack during sterilisation, storage and transportation and a clean peelability to allow an aseptic opening just before the use of the MD. The paper can be made compliant with ISO 11607-1 for international application and with complementary vertical parts EN 868 for European application.

By applying the sealing material 145, the paper web 120 is produced with on-line processing to create tamper evidence when the sealing is opened for enabling visual inspection that the package has kept its integrity so that the sterility of the MD can be verified until the end-use of the package. The tamper evidence may refer e.g. to visible transfer of some sealing material from the sealing layer to opposite material such as PE film or fibrous web. The transfer of the sealing material may be continuous over most or entire length of the sealing.

The paper machine 100 is capable of double side treating the paper web 120 online. The produced paper is made (e.g. heat) sealable and peelable on one side.

In this document, surface treatment and coating may be used interchangeably unless expressly otherwise stated, as the difference is often somewhat indefinite.

A skilled paper maker knows how to implement the normal parts of a paper machine that operate as known in the art. Hence, the structure and operation relating to surface treating of the paper web 120 will next be described in further detail. The example embodiment shown in FIG. 1 is used for illustrating some implementations.

FIG. 2 shows a medical sterilization packaging 200 with a medical device 220 therein, seen as a cross-section, with greatly exaggerated thicknesses for illustration purposes. FIG. 2 also demonstrates the reinforcing material 143 that has penetrated throughout the paper web from the first side 120a to the second side. FIG. 2 further demonstrates a peelable sealing layer 145 and a packaging element 210 that is here of flexible PE film that has been attached through its rims to the sealing layer 145 by sealing region 230.

The minimum value for seal strength for a medical packaging in healthcare facilities shall be 1.5 N/15 mm for steam sterilisation and 1.2 N/15 mm for other type of sterilisation when tested in accordance to EN 868-5 (2009) annex D. The medical sterilisation packaging is preferably produced accordingly.

FIG. 3 shows the medical sterilization packaging of FIG. 2 seen as from bottom. FIG. 3 shows clearly the sealing region 230 surrounding the packaged medical device 220. On peeling the packaging open, some of the sealing layer 145 will divide or transfer from the medical paper to the second web, so that even if the packaging element (PE film in this example) is glued back, continuous visible traces will be left as tamper evidence.

The reinforcing material 143 on the other hand provides the structure of the paper with greater delaminating resistance than what the paper experiences when the packaging is opened by peeling off the paper.

In an example embodiment, the amount and the dry content of reinforcing material applied on the first side 120a of the paper web 120 is varied depending on the material in question. For instance, the dry amount may range between 0.2 wt % to 8 wt % and the dry content can be 4 wt % to 20 wt %. The notation wt % refers to weight per cent or mass fraction i.e. the relation of weight of given component to total mass including the component in question when calculated for dry paper i.e. paper in balance moisture.

In an example embodiment, the produced paper has basis weight of 40 $g/m^2$ to 120 $g/m^2$, such as 63,5 $g/m^2$, when measured in balance moisture.

By measuring in balance moisture reference is made to normal paper testing conditions i.e. 23° C., 50% relative humidity, normal air pressure.

In an example embodiment, the sealing material is applied to the paper web in dry content of 35 wt % to 40 wt %.

Pulp

The paper pulp is made with cellulosic and optionally with up to 30 wt % of synthetic fibres such as synthetic staple fibres. It should be noticed that cellulosic does not refer to only chemical pulping but rather to fibres of cellulose and/or hemicellulose that can also be formed e.g. by mechanical pulping. In an example embodiment, the pulp is made with non-recycled i.e. virgin bleached pulp. The main constituents of the pulp are softwood (e.g. pine or spruce) and hardwood (e.g. birch, eucalyptus) 100 wt %-0 wt % versus 0 wt % to 100 wt %, preferably in a mixture of 20/80 to 50/50 distribution measured in dry weight between softwood and hardwood, respectively. This distribution refers to distribution of cellulosic fibres.

Wet End Considerations

The paper web or pulp can be processed by:
Sizing e.g. with rosin or alkyl ketene dimer (AKD) and/or alkenyl succinic anhydride (ASA)
Wet strength supporting by adding in the pulp e.g. polyacrylic ester (PAE) or polyacrylic acid ester (PAAE)
reinforcing e.g. by adding in the pulp e.g. starch; carboxyl methyl cellulose (CMC); and/or synthetic binder.

Surface Treatment Materials

The reinforcing material can be selected so that the paper gains sufficient delamination resistance considering the seal strength so that on peeling open a medical package comprising the paper, the paper would not delaminate such that the content of the package might be contaminated by torn fibres. Factors affecting to the selecting of the reinforcing material are the composition of the pulp, the wet end sizing level, the amount of the reinforcing material that is pressed into the structure of the paper web, the smoothness and porosity of the paper web on applying the reinforcing material, the viscosity of the reinforcing material and the pressing conditions in general. The reinforcing material can be selected e.g. from starch; polyvinyl alcohol (PVOH); synthetic binder such as Styrene Acrylic; Acrylic, Styrene Butadiene (SB), Acrylate Styrene Butadiene, Butyl acrylate Vinyl Acetate, carboxylated SB, Vinyl Acetate (VA), Vinyl acetate acrylique Acrylic, Vinyl acetate acrylate, Vinyl Chloride (VC), polyvinyl chloride (PVC), polyurethane; and any copolymer or combination thereof.

The heat-sealing material is selected according to the application to which the medical paper is being produced. In an example embodiment, the heat sealing material can be selected e.g. from ethylene vinyl acetate copolymer; ethylene acrylic acid copolymer; polyethylene copolymer wax; polypropylene wax; or any combination thereof. The heat-sealing material also comprises, in an example embodiment, thickener for increasing viscosity to 150-300 cps and keeping the treatment on the top of the sheet (CMC, starch, PVOH, synthetic thickener) i.e. avoiding penetration of the heat-sealing material into the structure of the paper web 120.

In one particular example embodiment, a medical package is manufactured as follows:
- Ready paper:
  - ISO 536 grammage=63,5 g/m$^2$
  - ISO 1924-2: tensile strength MD=6 kN/m
  - ISO 1924-2: tensile strength CD=2.8 kN/m
  - ISO 2758: Bursting strength=330 kPa
  - ISO 1974: Tear strength MD=455 mN
  - ISO 1974: Tear strength CD=540 mN
- Base paper
  - 60 g/m2 refined to 27° SR
  - 47.7 g/m$^2$ virgin, bleached hardwood: birch
  - 11.9 g/m$^2$ virgin, bleached hardwood: pine
  - 0.3 g/m$^2$ of adjuvants in the base for internal sizing, wet strength and fibre bonding
- Side 1: reinforcement treatment
  - dry content=5%
  - chemicals: starch+AKD 0.1 g/m$^2$
  - viscosity: adjusted to 20 cps with Brookfield 100T
  - dry coating weight=0.5 g/m$^2$
  - Application and pressing: Film transfer process e.g. with an online Sym-sizer station.
  - Smooth rod and polyurethane (PU) covered nip roll
- Side 2: Heat-sealing treatment:
  - Dry content=38%
  - chemicals: dispersion of EVAc+thickener CMC
  - Viscosity: adjusted to 180 cps with Brookfield 100T
  - Total dry coating weight=3 g/m$^2$
  - Process: Film transfer substantially simultaneously with the processing of side 1 with reinforcement material.
  - Grooved rod and PU covered nip roll
- Packaging:
  - the heat sealable side of paper is sealed against a medical polyethylene (PE) thermo-sealable film for medical packaging e.g. Steriking® ESE 12/50 (WIPAK®)
  - Sealing conditions: 150° C., 500 N/10 cm$^2$, 1 sec.
  - Seal strength: 2 N/15 mm
  - Peel quality: clean peel and tamper evidence In another particular example embodiment, a medical package is manufactured as follows:
- Ready paper:
  - ISO 536 grammage=88 g/m$^2$
  - ISO 1924-2: tensile strength MD=7.0 kN/m
  - ISO 1924-2: tensile strength CD=3.6 kN/m
  - ISO 2758: Bursting strength=370 kPa
  - ISO 1974: Tear strength MD=560 mN
  - ISO 1974: Tear strength CD=630 mN
- base paper=80 g/m$^2$ refined to 25° SR
  - 28 g/m$^2$ virgin, bleached hardwood: birch
  - 28 g/m$^2$ virgin, bleached hardwood: pine
  - 14 g/m$^2$ PET synthetic fibres 5 mm
  - 0.3 g/m$^2$ of adjuvants in the base for internal sizing, wet strength and fibre bonding
- Side 1: reinforcement treatment
  - dry content=45%
  - chemicals: Acrylic latex (Tg=−13° C.)
  - viscosity: 20 cps with Brookfield 100T
  - dry coating weight=10 g/m$^2$
  - Application and pressing: Film transfer process e.g. with an online twin HSM station.
  - Smooth rod and polyurethane (PU) covered nip roll
- Side 2: Heat-sealing treatment:
  - Dry content=38%
  - Chemicals: dispersion of EVAc+thickener: adjusted to 180 cps with Brookfield 100T
  - Total dry coating weight=8 g/m$^2$
  - Process: Film transfer substantially simultaneously with the processing of side 1 with reinforcement material.
  - Grooved rod and PU covered nip roll
- Packaging:
  - Seal/Peel: the heat sealable side of paper is sealed against a medical polyethylene (PE) thermo-sealable film for medical packaging e.g. Steriking® ESE 12/50 (WIPAK®).
  - Sealing conditions: 150° C., 500 N/10 cm$^2$, 1 sec.
  - Seal strength: 3.5 N/15 mm
  - Peel quality: clean peel and tamper evidence In one example embodiment, cold seal material is used rather than heat-sealing material for sealing the paper in the packaging. The pressure-sealing material is, for example, natural rubber.

Various embodiments have been presented. It should be appreciated that in this document, words comprise, include and contain are each used as open-ended expressions with no intended exclusivity.

The foregoing description has provided by way of non-limiting examples of particular implementations and embodiments of the invention a full and informative description of the best mode presently contemplated by the inventors for carrying out the invention. It is however clear to a person skilled in the art that the invention is not restricted to details of the embodiments presented in the foregoing, but that it can be implemented in other embodiments using equivalent means or in different combinations of embodiments without deviating from the characteristics of the invention.

Furthermore, some of the features of the afore-disclosed embodiments of this invention may be used to advantage without the corresponding use of other features. As such, the foregoing description shall be considered as merely illustrative of the principles of the present invention, and not in limitation thereof. Hence, the scope of the invention is only restricted by the appended patent claims.

The invention claimed is:

1. A method for manufacturing medical paper for medical sterilization packaging, the method comprising:
   forming a paper web of fibrous substrate comprising cellulosic fibres, the paper web comprising opposite first and second sides;
   on-line with the forming of the paper web, applying reinforcing material on the first side and pressing the reinforcing material into structure of the paper web such that delamination resistance of the structure is increased throughout the structure of the paper web; and on-line with the forming of the paper web, applying sealing material on the second side the paper web.

2. The method of claim 1, wherein the sealing material is applied as on the paper web by a method selected from the group consisting of film transfer, spray coating, air-doctor coating and curtain coating.

3. The method of claim 1, wherein the paper web is formed to contain internal sizing agent for decreasing water absorption.

4. The method of claim 3, wherein the internal sizing agent comprises at least one of rosin; alkyl ketene dimer; and alkenyl succinic anhydride.

5. The method of claim 1, wherein the paper web is formed to contain wet strength agent for increasing wet strength characteristics of the paper web.

6. The method of claim 5, wherein the wet strength agent comprises at least one of polyacrylic ester or polyacrylic acid ester.

7. The method of claim 1, wherein the applying of the reinforcing material and the applying of the sealing material are performed substantially simultaneously.

8. The method of claim 1, wherein the pressing is performed after the applying of the reinforcing material and the applying of the sealing material and before subjecting either of the first and second side to drying by any dryers.

9. The method of claim 1, further comprising applying reinforcing material onto the second side of the paper web on-line with the forming of the paper web and before the applying of the sealing material.

10. The method of claim 9, wherein the reinforcing material is applied substantially simultaneously on both the first and second side of the paper web.

11. The method of claim 1, wherein the pressing is performed by a nip of two rolls.

12. The method of claim 1, wherein the applying of the reinforcing material is performed by applying 0.3 dry wt % to 8 dry wt % of the reinforcing material on the first side before the pressing the reinforcing material.

13. The method of claim 1, wherein the sealing material is applied to the second side of the paper web by applying 2.5 wt % to 10 wt % of the sealing material.

14. The method of claim 1, wherein the sealing material is heat-sealing material, preferably comprising any one or more of the following: ethylene vinyl acetate copolymer; ethylene acrylic acid copolymer; polyethylene wax and copolymer; and polypropylene wax and copolymer.

15. The method of claim 14, wherein the viscosity of the heat-sealing material is adjusted before the applying on the second side of the web to 150 cps to 400 cps so as to prevent penetration of the heat-sealing material into the structure of the paper web.

* * * * *